United States Patent [19]

Kiyohara

[11] Patent Number: 5,331,688
[45] Date of Patent: Jul. 26, 1994

[54] DISPOSABLE FOOT WARMER

[76] Inventor: Takashi Kiyohara, 12-16, Tonoyama-cho, Nishinomiya-shi, Hyogo-ken, Japan

[21] Appl. No.: 30,842

[22] Filed: Mar. 12, 1993

[30] Foreign Application Priority Data

Mar. 27, 1992 [JP] Japan .................. 4-025917

[51] Int. Cl.$^5$ .................. A43B 7/02; A61F 7/08
[52] U.S. Cl. .................. 2/239; 36/2.6; 607/111
[58] Field of Search .......... 128/382, 383; 36/2.6; 2/239, 160, 241, 905, 1; 165/46; 126/269; 607/108-111

[56] References Cited

U.S. PATENT DOCUMENTS

| 103,061 | 5/1870 | Littlepage | 128/383 |
|---|---|---|---|
| 641,890 | 1/1900 | Prosser | 128/383 |
| 813,053 | 2/1906 | Marchand | 128/383 |
| 1,566,987 | 12/1925 | Simmons | 128/382 |
| 1,586,546 | 6/1926 | Wyeth | 36/2.6 |
| 1,741,340 | 12/1929 | Scholl | 2/239 |
| 2,444,098 | 6/1948 | Handfield | 128/383 |
| 3,334,356 | 8/1967 | Abel | 2/239 |
| 4,249,319 | 2/1981 | Yoshida | 36/26 |
| 4,894,931 | 1/1990 | Senee et al. | 36/2.6 |
| 5,084,986 | 2/1992 | Usui | 36/2.6 |

FOREIGN PATENT DOCUMENTS

| 967000 | 5/1975 | Canada | 36/2.6 |
|---|---|---|---|
| 276393 | 11/1949 | Switzerland | 36/2.6 |
| 16726 | of 1895 | United Kingdom | 128/383 |
| 136110 | 12/1919 | United Kingdom | 128/383 |

Primary Examiner—Clifford D. Crowder
Assistant Examiner—Amy B. Vanatta
Attorney, Agent, or Firm—John F. A. Earley; John F. A. Earley, III

[57] ABSTRACT

This invention relates to a disposable foot warmer comprising an inner bag capable of being applied to socks or stockings to warm a foot, and the inner bag is shaped so as to have an area and a thickness which does not protrude out of the plantar arch of a foot, so that the inner bag may be used as being applied to socks or stockings at their portion confronting the plantar arch.

4 Claims, 4 Drawing Sheets

DISPOSABLE FOOT WARMER

TECHNICAL FIELD

This invention relates to a disposable foot warmer which is capable of warming a foot when being applied to socks or stockings.

PRIOR ART

Previously, disposable foot warmers comprised a flexible thin inner bag made of materials having gas permeability and an outer bag made of materials having no gas permeability in which the inner bag was vacuum packaged. The inner bag contained a mixture of powders, main components of which were ferrous powders capable of generating heat when being oxidized with atmospheric oxygen and powders of pro-oxidants for the ferrous powders. Besides, the inner bag had a front side made of materials having gas permeability and a back side made of materials to which a layer of an adhesive was applied, and the surface of the layer of adhesive was releasably covered by a releasing paper. The inner bag to be taken out of the outer bag was a thin bag formed almost in the shape of a rectangle having the width of about 5.5 centimeters and the length of about 8.5 centimeters, and the largest thickness of the inner bag was about 0.7 cm. The inner bag was made so that it may warm a foot, when being applied to socks or stockings at their portion confronting so-called ball of the sole of a foot. However, the disposable foot warmers had drawbacks mentioned below.

Since the inner bag came in contact with the sole of a foot at its portion which was affected pressure, when a user who applied the inner bag to his socks or stockings put on shoes and walked, the user felt tight and uncomfortable, and he felt as if there was something in his shoes, and he was injured in the sole of his foot. Accordingly, it was difficult for the user to walk for a long time or to take hard exercise and work. Besides, the inner bag easily slipped off from the position at which it had been applied to, and the inner bag was easily removed from socks or stockings.

SUMMARY OF THE INVENTION

An object of this invention is to provide a disposable foot warmer comprising an inner bag which does not make a user feel tight and uncomfortable, which does not make a user feel as if there were something in his shoes, which does not hurt the sole of his foot, and which enables a user to walk for a long time and to take hard exercise or work, when the user puts on shoes and walks, after the inner bag has been applied to his socks or stockings.

To accomplish the foregoing object, this invention provides a disposable foot warmer comprising an inner bag capable of being used as being applied to socks or stockings to warm a foot, said disposable foot warmer characterized in that the inner bag is shaped so as to have an area and a thickness which do not protrude out of the space between the plantar arch of the foot and the insole of shoes, so that the inner bag may be used as being applied to socks or stockings at their portion confronting the plantar arch of the foot.

In the present invention, the inner bag is shaped like a half-moon or ellipse having an area which does not protrude out of the space of the plantar arch of the foot.

BRIEF DESCRIPTION OF THE DRAWINGS

In the accompanying drawings:

FIG. 3 is a diagram of a side view showing a working condition of the inner bag of the embodiment of FIG. 1, which is applied to socks at their portion confronting the plantar arch, as shoes are put on;

FIG. 4 is a diagram of a planar view showing a working condition of the inner bags of the embodiment of FIG. 1, which are applied to socks at their portion confronting the plantar arch and at their portion confronting a depressed portion between the tip of toes and the instep, as shoes are put on;

FIG. 7 is a diagram of a planar view showing a working condition of the inner bags of the embodiment of FIG. 5, which are applied to socks at their portion confronting the plantar arch and at their portion confronting a depressed portion between the tip of toes and the instep, as shoes are put on.

EXAMPLE 1

Figure 1:
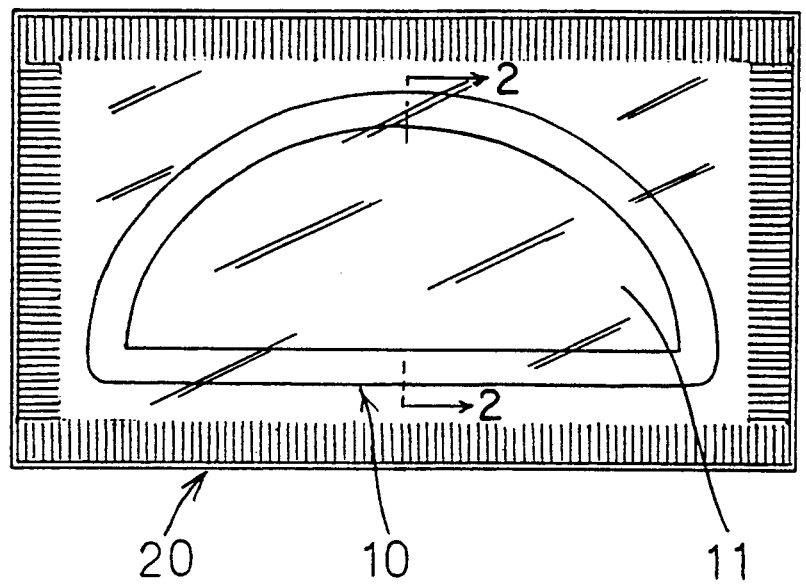
FIG. 1 is a planar view of an embodiment of a disposable foot warmer according to the present invention.

An embodiment according to the invention is shown in FIGS. 1 to 4.

A disposable foot warmer according to the embodiment comprises an inner bag 10 which contains a mixture of powders 15 comprising iron filings, moisture, salt, powders of activated carbon and wood flour and an outer bag 20 in which the inner bag 10 has been vacuum packaged.

The inner bag 10 comprises a front side made of a flexible non-woven fabric 11 having gas permeability and a back side made of a flexible non-woven fabric 12 to which a layer of an adhesive 13 has been applied, and which has no gas permeability. A releasing paper 14 is releasably affixed to the surface of the layer of the adhesive 13 applied to the back side of the flexible non-woven fabric 12.

The inner bag 10 is shaped like a half-moon which has the largest width of about 4.5 centimeters and the largest length of about 8.0 centimeters, and the thickness of the inner bag 10 is about 0.82 to 1.2 centimeters. The inner bag 10 has an area and a thickness which do not protrude out of the space of the plantar arch 41 of an adult foot 40.

Figure 3:
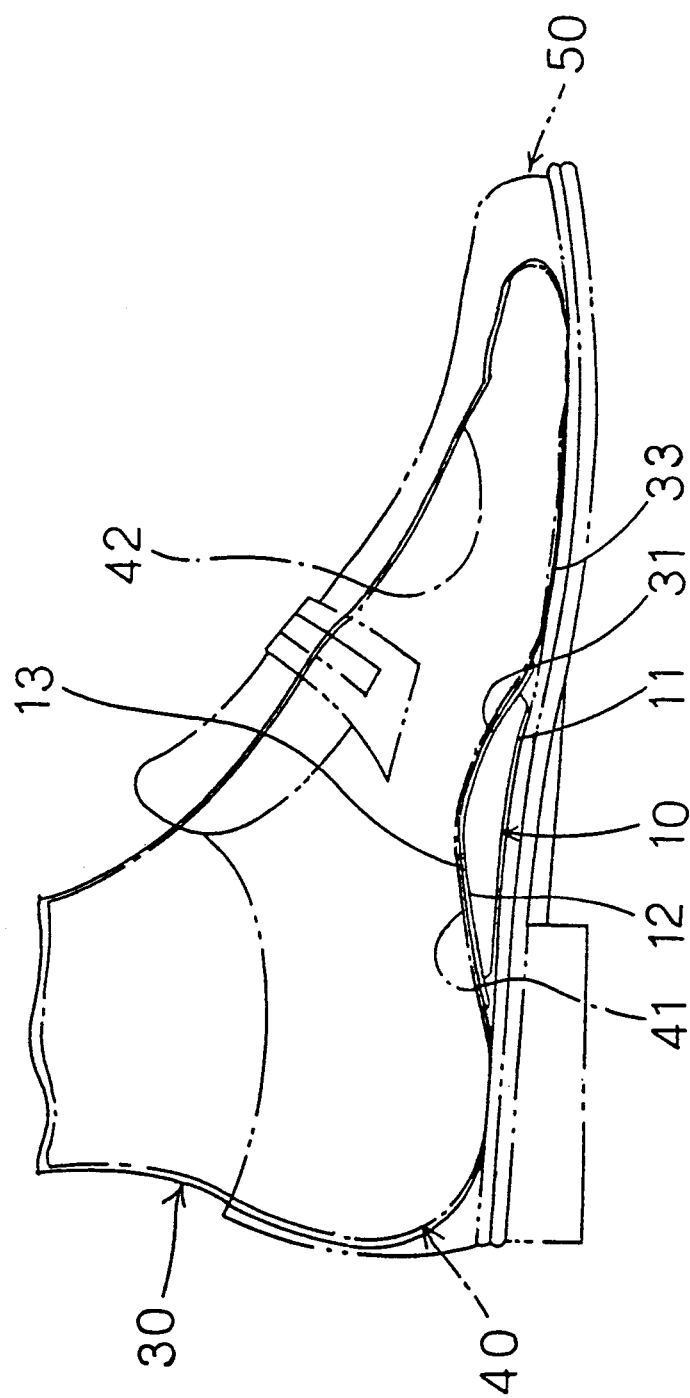

Because of the disposable foot warmer according to this embodiment being constituted as above-mentioned, after the outer bag 20 is teared to be opened, the inner bag 10 can be taken out of the outer bag 20. After the releasable paper 14 has been removed, as shown in FIGS. 3 and 4, the inner bag 10 is applied to socks 30 at their portion 31 confronting the plantar arch 41 of the foot 40, and then, shoes 50 are put on.

Figure 4:
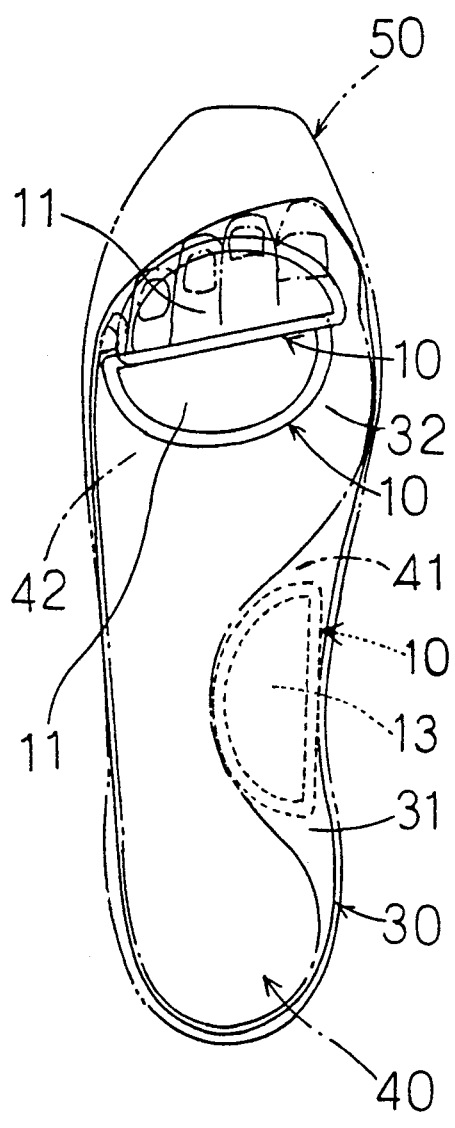

Besides, as shown in FIG. 4, the inner bag 10 may be applied to socks 30 at their portion 32 confronting a depressed portion 42 of a foot 40 between the tip of toes and the instep, and then, shoes 50 are put on.

The inner bag 10 applied to the portion 31 of socks 30 or the inner bag 10 applied to the portion 32 of socks 30 generates heat when the mixture of powders 15 are oxidized with air in the shoes 50. Thus, the inner bag 10 can warm the foot 40.

EXAMPLE 2

Figure 5:
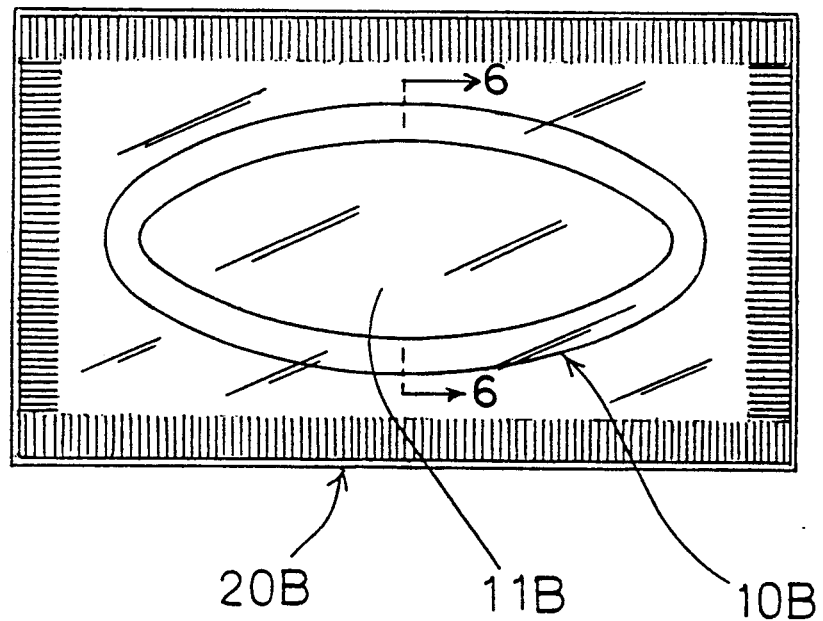
FIG. 5 is a planar view of another embodiment of a disposable foot warmer according to the present invention.
Figure 2:
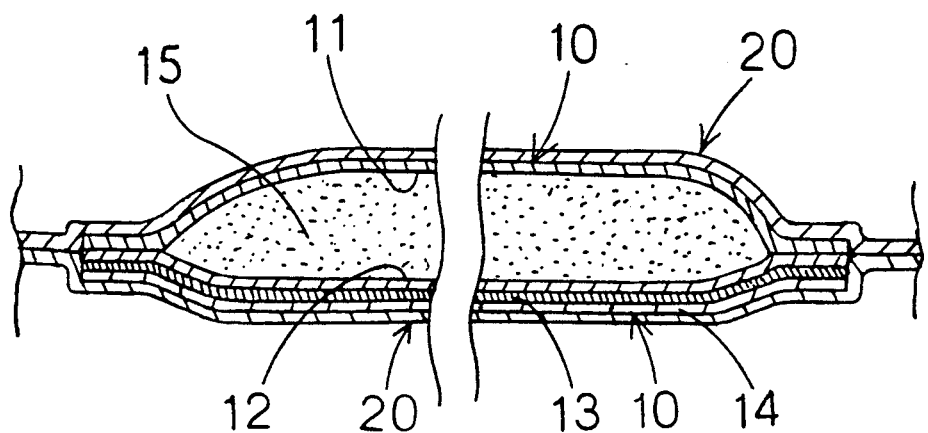
FIG. 2 is an enlarged sectional view showing the embodiment on the line A—A of FIG. 1, as the middle portion is omitted.
Figure 6:
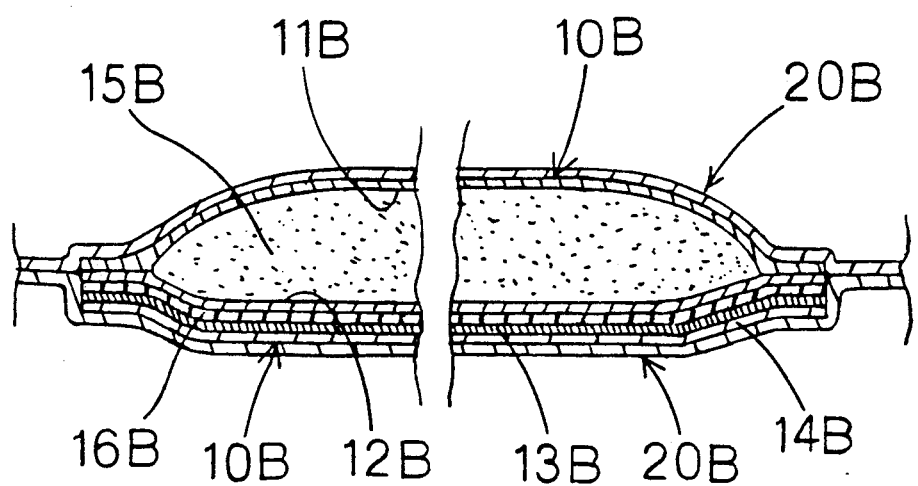
FIG. 6 is an enlarged sectional view showing the embodiment on the line B—B of FIG. 5, as the middle portion is omitted.
Figure 7:
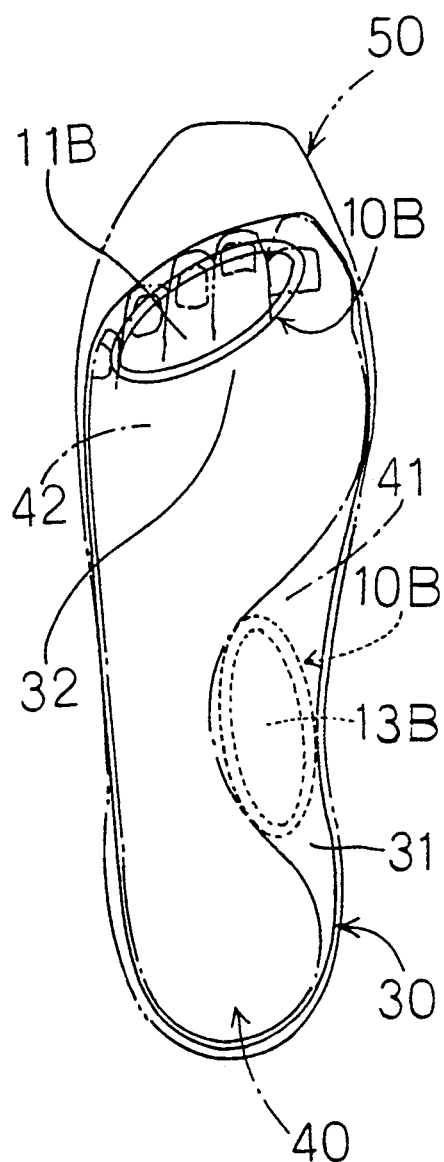

Another embodiment of the invention is shown in FIGS. 5-7.

A disposable foot warmer according to the embodiment comprises an inner bag 10B containing a mixture of powders 15B having the same composition as that mentioned in example 1 and an outer bag 20B in which the inner bag 10B has been vacuum packaged.

The inner bag 10B has a front side made of a flexible non-woven fabric 11B having gas permeability and a back side which comprises a flexible non-woven fabric 12B having no gas permeability, a sheet of foamed polyethylene 16B adhered to the non-woven fabric 12B and a layer of an adhesive 13B applied to the sheet 16B. A releasing paper 14B is releasably affixed to the surface of the layer of the adhesive 13B applied to the sheet of foamed polyethylene 16B. Since the sheet of foamed polyethylene 16B is adhered to the non-woven fabric 12B, it is possible for the temperature of the oxidation of the mixture of powders 15B to be sharply raised. In addition, the sheet 16B can prevent a user from getting burnt so called at low temperature, and the sheet 16B is useful for lessening undesirable feeling which the user feels when the mixture of powders 15B have formed a hard mass at the end of the reaction of the generation of heat.

The inner bag 10B is shaped like an elongated ellipse which has the length of about 8.5 centimeters and the width of about 3.5 centimeters, and the thickness of the inner bag 10B is about 0.51 to 0.91 centimeters. The inner bag 10B has an area and a thickness which do not protrude out of the space of the plantar arch 41 of an adult foot 40.

Since the disposable foot warmer according to this embodiment is constituted as above-mentioned, the inner bag 10B can be taken out of the outer bag 20B in which the inner bag 10B has been vacuum packaged. After the releasing paper 14B has been removed, as shown in FIG. 7, the inner bag 10B can be applied to soaks 30 at their portion 31 confronting the plantar arch 41 of an adult foot 40, and then shoes 50 are put on.

Besides, the inner bag 10B may be applied to socks 30 at their portion 32 confronting the depressed portion 42 of a foot 40 between the tip of toes and the instep, and then, shoes 50 are put on. The inner bag 10B applied to socks 30 at their portion 31 or the inner bags 10B applied to socks at their portions 31 and 32 generate heat when being oxidized with air in the shoes 50. Thus, the inner bag 10B can warm the foot 40.

EFFECT OF THE INVENTION

According to this invention, the inner bag 10 or 10B can be applied to socks or stockings 30 at their portion 31 confronting the plantar arch 41 of a foot 40, and if there is a surplus space in shoes, the inner bag 10 or 10B may be applied to socks or stockings 30 at their portion 32 confronting the depressed portion 42 of a foot 40 between the tip of toes and the instep.

Since the inner bag 10 or 10B applied to socks or stockings 30 at their portion 31 confronting the plantar arch 41 enters the space between the plantar arch 41 and an insole of shoes 50, it is possible for the inner bag 10 or 10B to be made with a considerable thickness, and the inner bag 10 or 10B does not make a user feel tight of his shoes during walking. In addition, since the inner bag 10 or 10B enters the space between the plantar arch 41 of a foot 40 and the insole of shoes 50, and since the inner bag 10 or 10B is not applied to socks or stockings 30, for instance, at their portion 33 confronting so called ball of the sole of a foot 40 which is affected pressure, the inner bag 10 or 10B does not make the user feel tight and uncomfortable, and the inner bag does not hurt the sole of a foot, and the inner bag does not make a user feel as if there were something in his shoes. Furthermore, the inner bag does not slip off from the position to which the inner bag has been applied, and the inner bag is not removed from socks or stockings. Thus, the inner bag can endure walks, works and exercises for a long time.

Furthermore, in case of well-fitted woman's shoes, the woman's shoes did not have surplus spaces which enabled prior disposable foot warmers to be applied to socks or stockings. However, the disposable foot warmers according to this invention can be used even when such well-fitted woman's shoes are put on, because the disposable foot warmer is intended to be applied to socks or stockings at their portion confronting the plantar arch of a foot so that the inner bag may enter the space between the plantar arch and the insole of shoes.

I claim:

1. A disposable foot warmer comprising a flexible inner bag which is made of materials having gas permeability and which contains a mixture of powders, main components of which are ferrous powders capable of generating heat when being oxidized with atmospheric oxygen and powders of prooxidants for the ferrous powders and an outer bag which is made of materials having no gas permeability and in which said inner bag has been vacuum packaged, said inner bag being capable of warming a foot as being applied to socks or stockings when the inner bag is generating heat, after the inner bag has been taken out of the outer bag, and after a releasing paper has been removed from the surface of a layer of an adhesive, said disposable foot warmer characterized in that the inner bag is shaped to have an area and a thickness which do not protrude out of the space between the plantar arch of a foot and an insole of shoes, so that the inner bag may be used as being applied to socks or stockings at their portion confronting the plantar arch of the foot, and that the inner bag has a front side made of materials having gas permeability and a back side made of materials which do not have gas permeability and to which a layer of an adhesive has been applied whereby to enable the inner bag to be applied to socks or stockings, so that heat emitted through the front side of the inner bag may warm air in the shoes and the insole of the shoes whereby to warm the whole foot, and so that heat conducted to the plantar arch through the back side of the inner bag may warm the sole of the foot.

2. A disposable foot warmer as claimed in claim 1, wherein the inner bag is shaped like a half-moon.

3. A disposable foot warmer as claimed in claim 1, wherein the inner bag is shaped elliptically.

4. A disposable foot warmer comprising a flexible inner bag which is made of materials having gas permeability and which contains a mixture of powders, main components of which are ferrous powders capable of generating heat when being oxidized with atmospheric oxygen and powders of pro-oxidants for the ferrous powders and an outer bag which is made of materials having no gas permeability and in which said inner bag has been vacuum packaged, said inner bag being capable of warming a foot as being applied to socks or stockings when the inner bag is generating heat, after the inner bag has been taken out of the outer bag, and after a releasing paper has been removed from the surface of a layer of an adhesive, said disposable foot warmer characterized in that the inner bag is shaped to have an area and a thickness which do not protrude out of the space between the plantar arch of a foot and an insole of shoes, so that the inner bag may be used as being applied to socks or stockings at their portion confronting the plantar arch of the foot, and that the inner bag has a front side made of materials having gas permeability and a back side made of materials which do not have gas permeability and which comprise a sheet of insulator and a layer of an adhesive applied to the sheet of insulator whereby to enable the inner bag to be applied to socks or stockings, so that heat emitted through the front side of the inner bag may warm air in the shoes and the insole of the shoes whereby to warm the whole foot, and so that heat conducted to the plantar arch through the back side of the inner bag may warm the sole of the foot without burning the plantar arch, whereby to enable the temperature to be raised in order to elongate the life of the disposable foot warmer.

* * * * *